(12) United States Patent
Schippers

(10) Patent No.: US 8,704,201 B2
(45) Date of Patent: Apr. 22, 2014

(54) FLEXIBLE ENERGY FILTER FOR ION BEAM THERAPY

(75) Inventor: Jacobus Maarten Schippers, Remigen (CH)

(73) Assignee: Paul Scherrer Institut, Villigen/PSI (CH)

( * ) Notice: Subject to any disclaimer, the term of this patent is extended or adjusted under 35 U.S.C. 154(b) by 0 days.

(21) Appl. No.: 13/512,670

(22) PCT Filed: Nov. 16, 2010

(86) PCT No.: PCT/EP2010/067540
§ 371 (c)(1),
(2), (4) Date: Dec. 11, 2012

(87) PCT Pub. No.: WO2011/064121
PCT Pub. Date: Jun. 3, 2011

(65) Prior Publication Data
US 2013/0137915 A1 May 30, 2013

(30) Foreign Application Priority Data

Nov. 30, 2009 (EP) .................................. 09177496

(51) Int. Cl.
*H01J 29/52* (2006.01)
(52) U.S. Cl.
USPC .................. 250/505.1; 250/515.1; 250/516.1; 250/518.1; 250/519.1

(58) Field of Classification Search
USPC ........... 250/505.1, 515.1, 516.1, 518.1, 519.1
See application file for complete search history.

(56) References Cited

U.S. PATENT DOCUMENTS

| 5,925,707 | A | * | 7/1999 | Shafer et al. ................... 524/490 |
| 6,703,632 | B1 | * | 3/2004 | Macklis et al. ............. 250/515.1 |
| 7,109,505 | B1 | * | 9/2006 | Sliski et al. ................ 250/505.1 |
| 7,560,715 | B2 | | 7/2009 | Pedroni |
| 2007/0034815 | A1 | | 2/2007 | Grozinger et al. |
| 2008/0023644 | A1 | | 1/2008 | Pedroni |

FOREIGN PATENT DOCUMENTS

| EP | 1740270 A1 | 1/2007 |
| WO | 2005/102453 A1 | 11/2005 |

* cited by examiner

*Primary Examiner* — Michael Maskell
(74) *Attorney, Agent, or Firm* — Laurence A. Greenberg; Werner H. Stemer; Ralph E. Locher

(57) ABSTRACT

An energy filter allows, particularly at lower beam energies, a determined spread of the beam energies in order to preserve the beam edges and to spread the Bragg peak at each individual beam energy. The energy filter behaves similarly to a ridge filter and spreads out the Bragg peak of a low energy proton beam (70-100 MeV) so that energy modulation of the beam can be done with steps of 5 mm in one go over the full range of 235-70 MeV. Due to its mechanical flexibility, the energy filter can be placed on the skin of the patient which minimizes the effect of scattering in the filter due to the short distance behind a layer of a plurality of metal particles within a flexible soft plastic sheet to the skin of the patient.

2 Claims, 4 Drawing Sheets a)

b)

FLEXIBLE ENERGY FILTER FOR ION BEAM THERAPY

BACKGROUND OF THE INVENTION

Field of the Invention

The present invention relates to a flexible energy filter for ion beam therapy. Further, the present invention relates to the use of said flexible energy filter within a gantry or fixed beam line for proton beams or ion beams. Furthermore, the present invention relates to a method for increasing the energy spread within a proton or ion beam for therapy before the beam enters a tissue.

In radiation therapy with proton or ion beams (hadron therapy), the penetration depth of the particles into the patient's tissue depends on the energy of the particles upon entering the tissue. The dose distribution as a function of depth is characterized by a Bragg curve: a dose that is more or less constant with depth, but that increases in the last 1-2 cm before the particles stop at the end of their range. The width of this Bragg peak is partly determined by the energy spread in the ion beam that enters the patient and is usually too narrow to be used directly for a tumor irradiation. Therefore, as illustrated in FIG. 1 left, the Bragg peaks are distributed over the tumor thickness (target region) by "stacking" curves with different ranges (i.e. using different energies). This stacking creates a high dose region of the same thickness at the tumor thickness. The right pictures of FIG. 1 shows the impact on the Bragg peak shape from the location of the energy modulation. Top diagram illustrates the energy modulation in the nozzle, bottom diagram illustrates the energy modulation in the beam line, followed by an analyzing system.

This range modulation, or actually energy modulation, can be done in the last part (nozzle) of the beam transport system. This part can also be mounted on a rotating beam transport system (also called gantry) that allows adjustment of the direction of the proton beam or ion beam onto the patient. One can e.g. insert a rotating wheel of plexiglass with an azimuthally varying thickness into the beam path, or insert a varying number of plexiglass plates into the beam path (FIG. 1 top). By inserting sheets of 5 mm thickness into the beam path, the Bragg peak in the tissue is pulled forward in 5 mm steps (FIG. 1, top right). Since the energy spread within the original beam before the modulation wheel or plates is constant, the shape of the Bragg peak does not change; only its position in depth changes.

When range modulation is performed in the particle accelerator or with a degrader immediately behind the accelerator, the absolute energy spread within the beam that reaches the patient will be lower with decreasing beam energy, compared to a system with a range modulation in the nozzle. Therefore, the Bragg peak becomes sharper at lower energies, as shown in FIG. 1, bottom, right. This method will be used at the Gantry-2 installation at the Paul Scherrer Institut, CH-5232 Villigen, but can also be applied at other gantries or fixed beam lines employing up stream energy modulation.

The sharp Bragg peak at rather lower beam energies can be beneficial when sharp edges of dose distributions are needed. However, when Bragg curves need to be stacked, a sharper Bragg peak would need more Bragg curves (i.e. beam energies) to obtain the desired depth dose distribution. This starts to be a problem when applying beam energies below ~100 MeV. This problem can be dealt with by several methods.

A first solution provides a range shifter (a graphite or plexiglass plate) of sufficient thickness to stop 100-110 MeV protons that is inserted into the nozzle, and uses e.g. 100-110 MeV as lowest proton-beam energy from the accelerator or degrader. In that case the Bragg peak is still broad enough to allow ~5 mm steps in range modulation.

Alternatively, or in combination with the range shifter, a ridge filter can be inserted into the nozzle to broaden the Bragg peak. This ridge filter is a plexiglass (or other material) layer, with deep groves and ridges. Particles that cross this plate, traverse different material thicknesses, and hence increase the energy spread in the beam leaving this filter, so that the Bragg peak width is increased in the patient. This method is also applied in nozzles for Carbon ion treatments.

BRIEF SUMMARY OF THE INVENTION

Both methods have the same disadvantages. Due to mechanical constraints, there will be some distance between the range shifter/ridge filter and the patient. This will cause lateral smearing of the beam due to multiple scattering in the range shifter/ridge filter, which causes unsharp dose distribution edges. Further, the treatment planning (dose calculations) and treatment session have to be split into two different parts (with and without range shifter).

It is therefore the objective of the present invention to provide an energy filter system that allows particularly at lower beam energies a determined spread of the beam energies in order to spread the Bragg peak and at the same time to preserve the sharpness of the lateral beam edges at each individual beam energy.

This objective is achieved according to the present invention by a flexible energy filter for particle beam therapy, comprising:
a) a cushion of plastic or water equivalent material (4) or a stack of two soft sheets of plastic or water equivalent material (4); and
b) attached to the surface of the cushion or to the surface of a soft sheet of plastic or water equivalent material, or embedded in the cushion or between the two soft sheets of plastic or water equivalent material (4), a layer (6) of a plurality of metal particles (8), preferably metal spheres; said layer (6) having a cross sectional area corresponding at least to a cross section of a beam scanning area at an outlet of the particle beam equipment prior to its entry into a tissue.

This energy filter behaves similar to a ridge filter and spreads out the Bragg peak of a low energy proton beam (70-100 MeV) so that energy modulation of the beam can be done with steps of 5 mm in one go over the full range of 235-70 MeV. Due to its mechanical flexibility, the energy filter can be placed on the skin of the patient which minimizes the effect of scattering in the filter due to the short distance behind the layer of the plurality of metal particles within the flexible soft plastic sheet (the flap) to the skin of the patient.

Typically, the soft plastic sheet may have a thickness in the range from 2 to 15 mm, preferable 3 to 8 mm, wherein the metal particles having a maximum size of less than 2 mm, preferably less than 1 mm. This particle size ensures therefore to be small enough that eventual shadows or dose inhomogeneities shortly behind the flap due to multiple scattering in the particles, e.g. spheres, will wash out. and to have on the other hand the a minimum size required to actually obtain a sufficient energy decrease.

In order to further reduce shadow effects of the particles in the dose distribution, the layer of a plurality of metal particles may be disposed in an asymmetrical plastic layer as seen in the direction of the propagation of the ion beam or proton beam. The asymmetry refers to a difference in thickness of the plastic layer at the exit of the soft plastic sheet as compared to the thickness at the entry of ion beam or proton beam into the soft plastic sheet.

In order to achieve the desired energy spread, the layer of metal particles may comprise particles of high density material, such as lead, of different sizes and/or a mixture of particles of equal size or different size but different composition, such as lead, copper and tungsten. The amount of particles per unit of layer area is derived from the desired shape of the widened Bragg peak. The location of the particles in the layer might be randomly distributed to prevent regular shadow patterns in the dose distribution behind the particles.

Typically, the soft plastic sheet may consist of standard bolus material used in radiation therapy, like e.g. the commercially available Superflab, which consists of a synthetic oil gel embedded in vinyl plastic. This material is enough flexible to enable the soft plastic sheet to fit as best as possible to the patient's body contour and to keep its thickness uniform at the desired thickness.

Further embodiments of the present invention now comprise the use of an energy filter according to the present invention within a proton or ion gantry or fixed beam line, at which said filter being mounted downstream of its outlet nozzle.

With respect to a method for obtaining an energy spread within a proton beam or ion beam before it enters a tissue, an inventive solution provides a method for an energy spread within a proton beam or an ion beam used for radiation therapy before it enters a tissue, wherein a gantry or a fixed beam line in combination with a patient positioning system is provided to produce the ion or proton beam at the desired direction, flux and energy, and an energy filter according to the present invention is provided upstream of the tissue proximate to the tissue.

BRIEF DESCRIPTION OF THE SEVERAL VIEWS OF THE DRAWING

Preferred embodiments of the present invention are hereinafter described with reference to the following drawing which depicts in.

DESCRIPTION OF THE INVENTION

Figure 1:
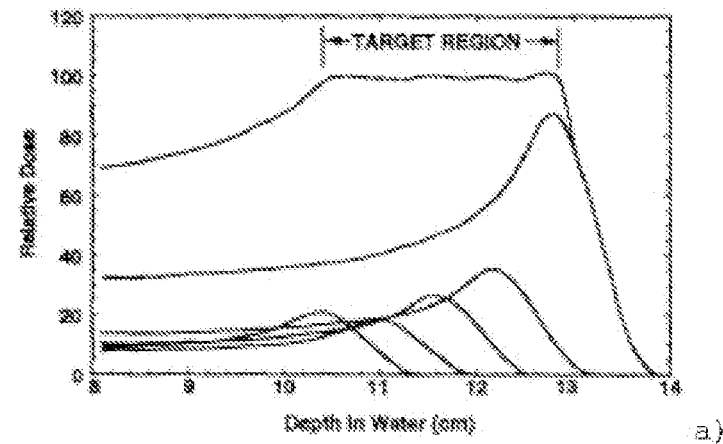
FIG. 1 a schematic illustration on the Bragg curves of different range being stacked to create a desired high dose region.
Figure 1:
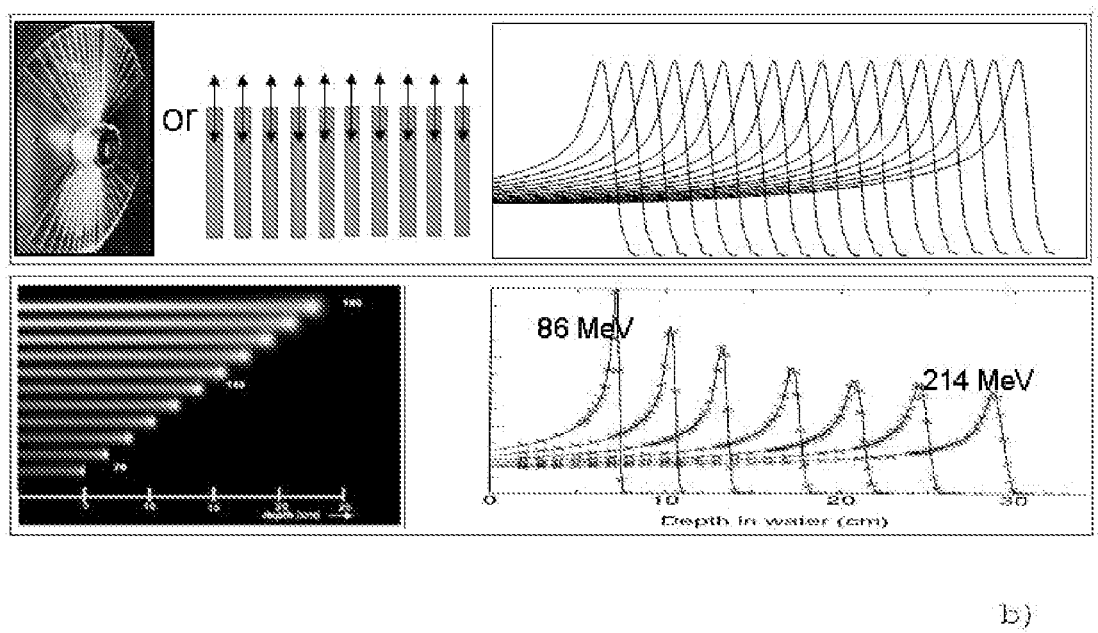
Figure 2:
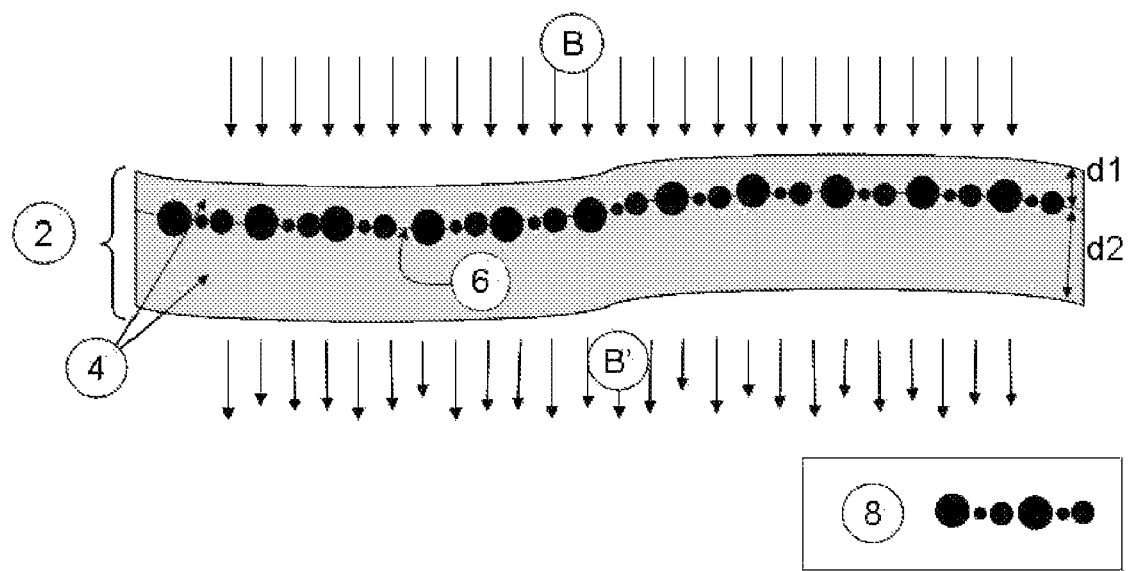
FIG. 2 a schematic cross-sectional view, not to scale, of an energy filter.

The present invention provides a flexible energy filter or energy spreading system, 2 in FIG. 2, for an ion therapy, such as proton therapy. One of the most modern proton therapy installations is disclosed in the European Patent Application 1 740 270 which is incorporated herewith by reference. Said proton therapy installation currently works at the Paul Scherrer Institut as "Gantry 2" facility. The flexible energy filter 2 that can be for example also used with this installation, is shown in FIG. 2 and is built as a stack 4 of two soft plastic sheets of 30×30 cm$^2$ (or any other suitable size) with a layer 6 of spheres 8 of heavy material in between the sheets. Similar as in a ridge filter, it spreads out the Bragg peak of a low energy proton beam (70-100 MeV) so that energy modulation of the beam can be done with steps of 5 mm in one go over the full range of 235-70 MeV. As shown in FIG. 2, the soft and flexible plastic flap 4 has ~5 mm thickness and encloses an embedded layer 6 of metal spheres 8. The big advantage of the present invention is that the flap 4 is so flexible that it can be put on the skin of a patient (not shown). Of course, this energy filter 2 could be also mounted easily (e.g. rolled up) in a nozzle. For different energies or modulation widths, different energy filters can be designed.

When the energy filter flap 2 is put on the skin of the patient, the effect of scatter in the energy filter 2 is minimized due to the short distance behind the flap 4. Therefore, the edges of the dose distribution are sharper than those obtained by the conventionally applied methods.

The spheres 8 are either spheres of high density material (e.g. lead) of different sizes as shown in the layer 6 of FIG. 2, or a mixture of spheres of equal size or different size but different composition, such as tungsten, lead, copper. Also wires or other shapes could be used. The spheres 8 are embedded in a layer 6 between two sheets of the soft material 4. As for an alternative, the spheres 8 could be also disposed on a cushion of plastic or water equivalent material. The spheres 8 could also be disposed within the cushion, i.e. the spheres 8 are molded in the structure of the cushion or the flexible sheet.

To reduce shadow effects of the spheres (8) in the dose distribution, the spheres 8 are rather small (≤1 mm). It can be an advantage to have a thicker plastic layer at the exit which is also illustrated in FIG. 2. The original beam B passes through the flap 4 and its energy is spread due to the layer 6 of metal spheres 8. In FIG. 2 the energy spread in the modified beam B' is illustrated by the different lengths of the arrows used to represent the modified B' as compared to the beam B where the arrow are shown at equal length. Thereby, a first distance d1 from the entry side of the energy filter 2 to the layer 6 is chosen to be different (in the figure an example is given where this is twice as small) as a second distance d2 from the layer 6 to the exit side of the energy filter 2.

Various simulation and measurements with different geometries of the spheres 8 have been performed to find out the optimal distribution and composition of the spheres 8. Typically, the spheres 8 must be so small that eventual shadows or dose inhomogeneities shortly behind the energy filter 2 due to multiple scattering in the spheres 8 will wash out. On the other hand the spheres 8 need a minimum size to obtain a sufficient energy decrease.

Figure 3:
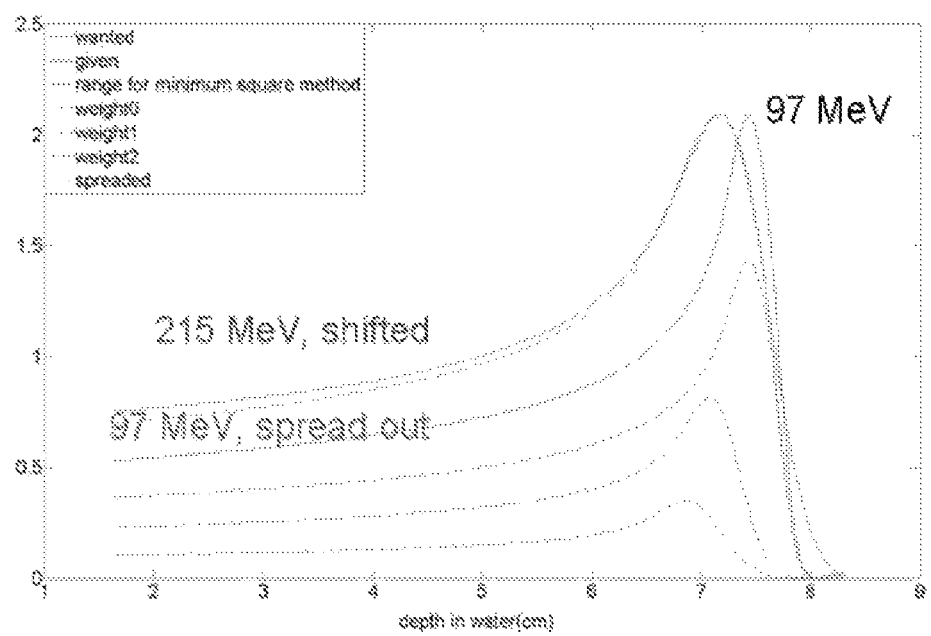
FIG. 3 a schematic illustration of the various Bragg curves to illustrate the effect of the energy filter of FIG. 2.

Computer simulations with a very simple model have shown encouraging results. A modulation with three weights has been made to spread a 97 MeV Bragg curve to the same shape as a 215 MeV Bragg curve. The largest weight is obtained by 4 mm water equivalent thickness, the middle weight by 1 mm (Ø) spheres of copper and the smallest weight by 1 mm (Ø) spheres of tantalum. In the simulation both spheres have been embedded in 4 mm water (simulating the plastic layers). FIG. 3 shows the broadened Bragg curve, compared to the one of 215 MeV, which shows the Bragg curves of 97 MeV, "monoenergetic", spread out and the 215

MeV Bragg curve that served as the desired shape. The three dashed lines represent the three components of the spread out curve.

Figure 4:
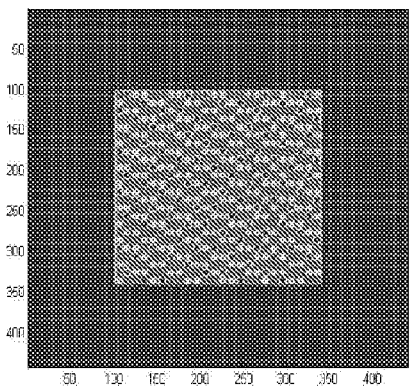
FIG. 4 a schematic view on the particle distribution in a plane transversal to the beam direction, made visible from the dose calculation by neglecting lateral scattering of the proton beam.

FIG. 4 illustrates the calculated dose distribution in a plane transversal to the beam direction, at 6.9 cm depth in a water phantom. In the calculation the lateral scattering in the water phantom has been suppressed to visualize the pattern of the spheres in the filter. FIG. 4 shows how the spheres (8) may be distributed, the dark spots represent the tantalum spheres and the light spots the copper spheres. In this example simulation the locations of the spheres were not randomly distributed within the layer (6). When neglecting the transversal scattering of the protons in the water phantom, as performed in this simulation, an image of the spheres 8 in the layer 6 becomes clearly visible at the depth of the maximum range of the spread-out Bragg peak.

Figure 5:
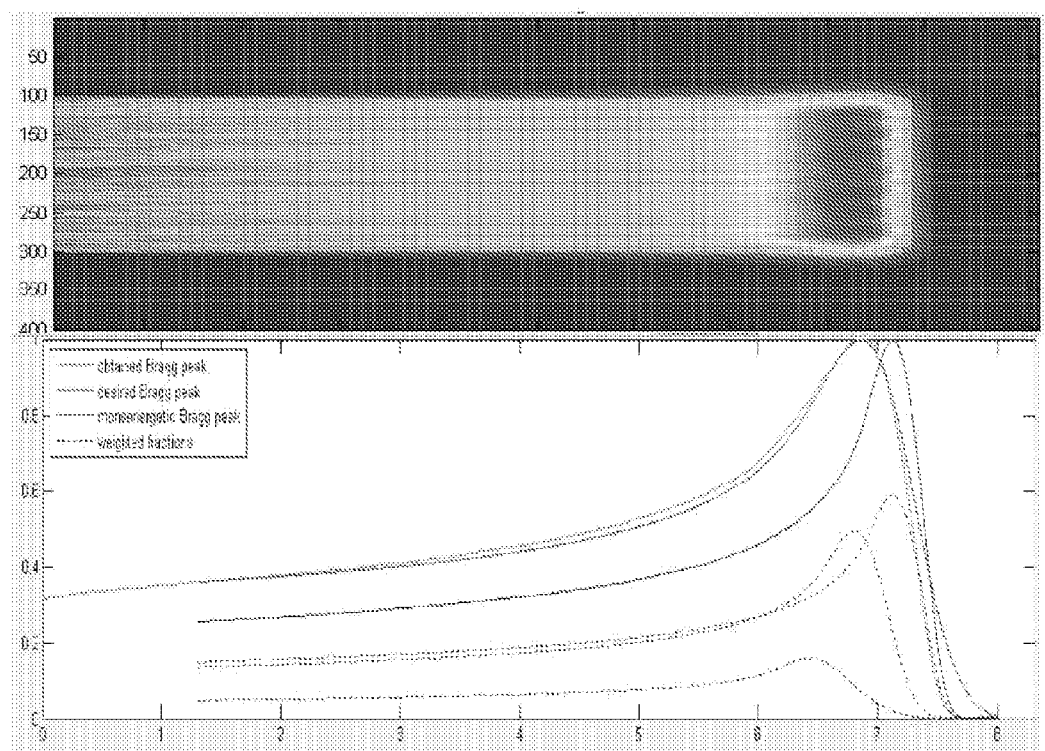
FIG. 5 a schematic view on the dose distribution as a function of depth in a water phantom.

FIG. 5 shows a dose distribution as a function of depth in a water phantom, starting 10 mm behind an energy filter composed of tungsten spheres of 1 and 0.5 mm in diameter. The bottom image shows the depth-dose profile or longitudinal dose profile. This has been obtained by integrating over the transversal dimensions.

Figure 6:
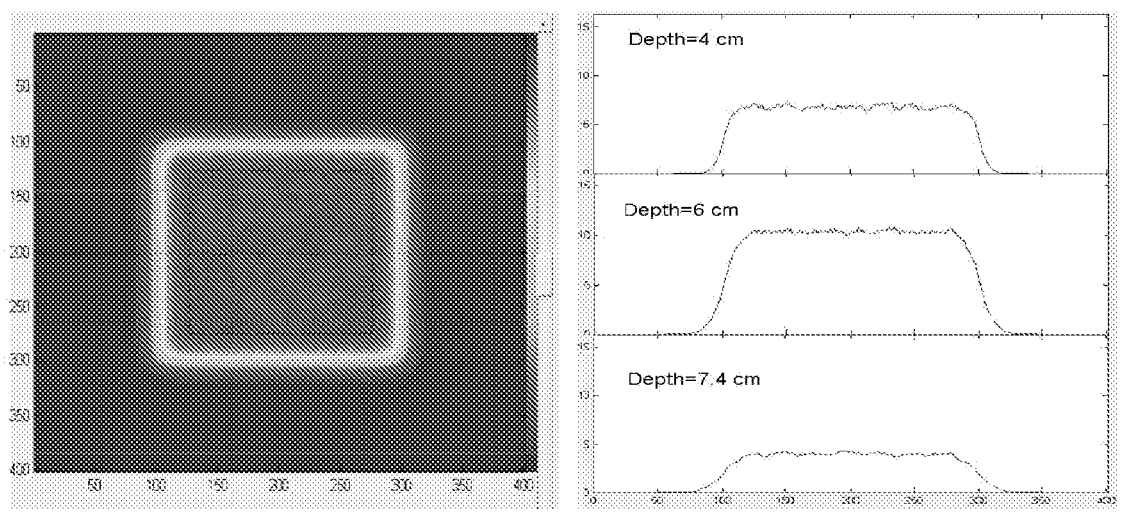
FIG. 6 a schematic view on dose distributions in a plane transversal to the beam direction at 6 cm depth in a water phantom.

FIG. 6 depicts a dose distribution in a plane transversal to the beam direction, at 6 cm depth in a water phantom, starting immediately behind an energy filter composed of tungsten spheres of 1 and 0.5 mm in diameter. The right image represents the transversal dose profiles at 4 cm, 6 cm and 7.4 cm depth. FIG. 6 (left) shows the transversal dose distribution at 10 mm depth in a water phantom, starting at 0 mm downstream of the energy filter and the transversal profiles at three different depths.

The figures show that the dose distribution is very homogeneous; the relative standard deviation of the dose is between 1.6% and 4%, depending on the depth and determined with a pixel size of 0.1 mm. For 1 mm resolution, this would imply a standard deviation between 0.5 and 1.3%.

The invention claimed is:

1. In combination with a proton or ion gantry or a fixed beam line having a beam outlet nozzle, an energy filter disposed on a patient downstream of the outlet nozzle, said energy filter comprising:
   a flexible carrier formed of a cushion of plastic or water equivalent material or a stack of two or more soft flexible sheets of plastic or water equivalent material; and
   a layer of a plurality of metal particles in or on said flexible carrier, said layer being attached to a surface of, or embedded in, the cushion or the soft sheet of plastic or water equivalent material;
   said layer having a cross sectional area corresponding at least to a cross section of a beam scanning area at an outlet of the particle beam equipment prior to an entry into a patient's tissue.

2. A method for an energy spread within an ion beam therapy for a tissue, the method which comprises:
   providing an energy filter for particle beam therapy, the energy filter including:
   a flexible carrier formed of a cushion of plastic or water equivalent material or a stack of two or more soft flexible sheets of plastic or water equivalent material; and
   a layer of a plurality of metal particles in or on the flexible carrier, the layer being attached to a surface of, or embedded in, the cushion or the soft sheet of plastic or water equivalent material, and the layer having a cross sectional area corresponding at least to a cross section of a beam scanning area at an outlet of the particle beam equipment prior to an entry into a patient's tissue;
   providing a gantry or a fixed beam line to produce a proton beam or an ion beam in a desired direction; and
   placing the energy filter as a cover of a patient's tissue and adapting a shape of the energy filter to a contour of the patient.

* * * * *